US00PP12290P2

(12) United States Plant Patent
Strope

(10) Patent No.: US PP12,290 P2
(45) Date of Patent: Dec. 18, 2001

(54) PETUNIA PLANT NAMED 'BALRUFVEIN'

(75) Inventor: Kerry Strope, Pismo Beach, CA (US)

(73) Assignee: Ball Floraplant, A Divison of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/475,952

(22) Filed: Dec. 31, 1999

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—June Hwu
(74) *Attorney, Agent, or Firm*—C. A. Whealy

(57) ABSTRACT

A new and distinct cultivar of Petunia plant named 'Balrufvein', characterized by its light purple with dark veined double flowers; mounded and eventually trailing plant habit; and very freely basal-branching habit.

1 Drawing Sheet

BACKGROUND OF THE INVENTION

The present invention relates to a new and distinct cultivar of Double Petunia plant, botanically known as *Petunia×hybrida*, and hereinafter referred to by the cultivar name Balrufvein.

The new Petunia is a product of a planned breeding program conducted by the Inventor in Arroyo Grande, Calif. The objective of the breeding program was to develop new Petunia cultivars with large double flowers; freely-branching vigorous growth habit; and attractive flower and foliage colors.

The new Petunia originated from a cross made by the Inventor of an unidentified selection of *Petunia×hybrida* described as a double white-flowered selection, as the male, or pollen parent, with the proprietary selection of *Petunia×hybrida* identified as code number 3404-4 as the female, or seed parent. The cultivar Balrufvein was discovered and selected by the Inventor as a flowering plant within the progeny of the stated cross in a controlled environment in Arroyo Grande in 1998. Plants of the new Petunia and a sibling cultivar, Balrufbrip (U.S. Plant Patent application filed concurrently with this application), differ primarily in flower color.

Asexual reproduction of the new cultivar by terminal cuttings taken at Arroyo Grande, has shown that the unique features of this new Petunia are stable and reproduced true to type in successive generations of asexual reproduction.

SUMMARY OF THE INVENTION

The following traits have been repeatedly observed and are determined to be the unique characteristics of 'Balrufvein'. These characteristics in combination distinguish 'Balrufvein' as a new and distinct cultivar:

1. Light purple with dark veined double flowers.
2. Mounded and eventually trailing plant habit.
3. Very freely basal-branching habit.

The new Petunia can be compared to the cultivar, Cascadia Double Pink, not patented. However, in side-by-side comparisons conducted by the Inventor in Arroyo Grande, plants of the new Petunia differ from plants of the cultivar Cascadia Double Pink in the following characteristics:

1. Plants of the new Petunia are taller and more vigorous than plants of the cultivar Cascadia Double Pink.

2. Stem and foliage colors of plants of the new Petunia are lighter green than stem and foliage color than plants of the cultivar Cascadia Double Pink.

3. Plants of the new Petunia have much larger flowers than plants of the cultivar Cascadia Double Pink.

4. Flower color of plants of the new Petunia is slightly darker than flower color of plants of the cultivar Cascadia Double Pink.

BRIEF DESCRIPTION OF THE PHOTOGRAPH

The accompanying photograph illustrates the overall appearance of the new cultivar as true as it is reasonably possible to obtain in colored reproductions of this type. Colors in the photographs may differ slightly from the color values cited in the detailed botanical description which more accurately describe the actual colors of the new Petunia. The photograph comprises a side perspective view of a typical flowering plant of 'Balrufvein'.

DETAILED BOTANICAL DESCRIPTION

The cultivar Balrufvein has not been observed under all possible environmental conditions. The phenotype may vary somewhat with variations in environment such as temperature and light intensity, without, however, any variance in genotype. The following observations and measurements describe plants about 10 weeks after planting rooted cuttings and grown in 10-cm pots in West Chicago, Ill., under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Petunia×hybrida* cultivar Balrufvein.

Parentage:

*Male parent.*—Unidentified selection of *Petunia×hybrida*, described as a double white-flowered selection, not patented.

*Female parent.*—Proprietary selection of *Petunia×hybrida* are identified as code number 3404-4, not patented.

Propagation:

*Type cutting.*—Terminal cuttings.

*Time to initiate roots.*—About 7 days with 18° C.

*Time to develop roots.*—About 21 days with 18° C.

*Root description.*—Fibrous, fine, freely branching.

Plant description:

*Form.*—Indeterminate; mounded and eventually trailing.

*Growth and branching habit.*—Vigorous. Very freely basal-branching; typically about 16 lateral branches per plant; pinching enhances branching. Appropriate for 10 to 15-cm containers and hanging baskets.

*Crop time.*—About 8 to 10 weeks are required to produce a finished flowering plant from a rooted cutting.

*Plant height* (*from soil level to top of plant plane*).—About 20.8 cm.

*Area of spread.*—About 26.9 cm.

*Lateral branches.*—Length: About 20 cm. Diameter: About 3 mm. Internode length: About 1.8 cm. Texture: Pubescent, glandular; viscid. Color: 144A.

*Foliage description.*—Leaves simple, generally symmetrical and long persisting. Leaf arrangement alternate before flowering, opposite after flowering. Quantity per lateral branch: About 14. Length: About 3.7 cm. Width: About 2.5 cm. Shape: Elliptic. Apex: Broadly acute. Base: Obtuse. Margin: Entire. Texture: Pubescent on both surfaces, velvety; viscid. Color: Young foliage, upper surface: 137B. Young foliage, lower surface: 137D. Mature foliage, upper surface: 137A. Mature foliage, lower surface: 137C. Venation, both surfaces: 146C. Petiole: Length: About 6 mm. Diameter: About 2 mm. Color: 144C.

Flower description:

*Flower type and habit.*—Light purple with dark veins; double flowers; salverform; flowers face outward; single, axillary. Flowers persistent. Flowering continuous. Not fragrant.

*Natural flowering season.*—Long day responsive; flowering from spring through fall.

*Quantity.*—Freely flowering with about 64 flower and flower buds per plant.

*Flower buds* (*showing color*).—Length: About 4 cm. Diameter: About 1.1 cm. Shape: Linear to funnel-shaped. Color: 76A.

*Corolla.*—Arrangement/appearance: Outer whorl of about five petals, fused into a flared trumpet, ruffled; typically more than 12 inner petaloids; petaloids irregular in shape and size. Flower diameter: About 7.3 cm. Flower tube length: About 5.3 cm. Flower throat diameter, distal end: About 1.8. Flower tube diameter, proximal end: About 1.2. Petal length from throat: About 3 cm. Petal width: About 3.5 cm. Petal shape: Roughly spatulate, fan-shaped. Petal apex: Rounded. Petal margin: Entire, somewhat undulate. Texture: Smooth, dull; viscid. Color: When opening, upper surface: Closest to 82 C. When opening, lower surface: Close to 76B. Opened flower, upper surface: 75A; midvein and larger veins, 77A; smaller lateral veins, 60C. Open flower, lower surface: Between 76C and 84D; veins, 83C. Flower throat (inside): 79C; veins, 77A. Flower tube (outside): 76C; main vein, 146C, others, 83C.

*Sepals.*—Quantity/arrangement: Five; not imbricate. Shape: Oblong. Apex: Rounded. Margin: Entire. Aspect: Upright. Texture: Pubescent, velvety. Color: Upper surface: 137A. Lower surface: 137C.

*Peduncle.*—Strength: Moderately strong. Angle: About 45° to stem. Length: About 4 cm. Color: 144A.

*Reproductive organs.*—Stamens: Stamen number: About 10, some fused to petaloids. Stamen length: About 1.2 cm. Stamen color: 8D with streaks of 72A. Anther shape: Oval. Anther length: About 4 mm. Anther color: Closest to 8D. Pollen amount: Moderate. Pollen color: Close to 97D. Pistils: Pistil length: About 2 cm. Style color: 144D. Stigma color: 144B, slightly overlaid with 86B. Ovary color: 143C.

*Seed.*—Seed production has not been observed.

Disease resistance: Plants of the new Petunia have not been observed to be resistant to pathogens common to Petunia.

It is claimed:

1. A new and distinct cultivar of Petunia plant named 'Balrufvein', as illustrated and described.

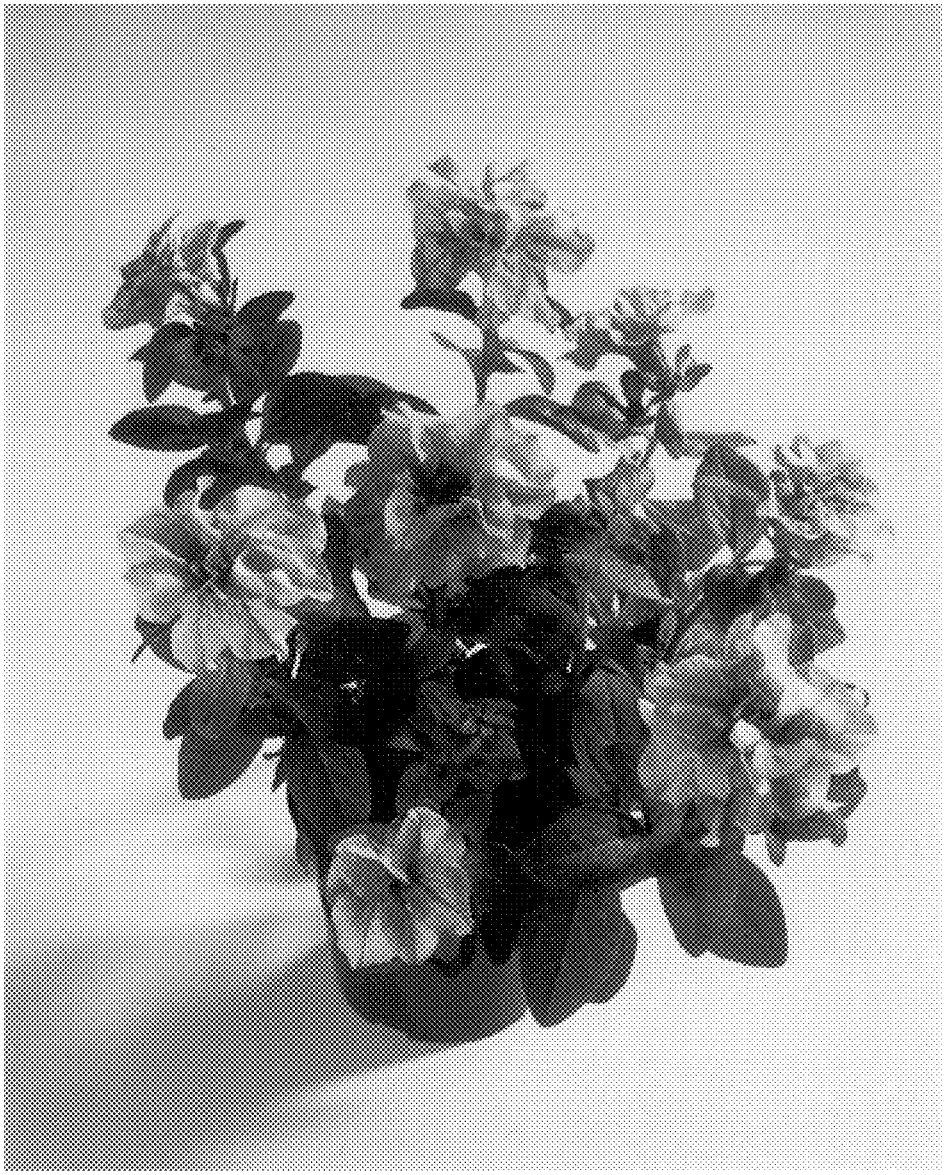

* * * * *